United States Patent [19]

Francoeur et al.

[11] Patent Number: 5,196,410
[45] Date of Patent: Mar. 23, 1993

[54] TRANSDERMAL FLUX ENHANCING COMPOSITIONS

[75] Inventors: Michael L. Francoeur, East Lyme; Russell O. Potts, Old Saybrook both of Conn.

[73] Assignee: Pfizer Inc., New York, N.Y.

[21] Appl. No.: 759,705

[22] Filed: Sep. 11, 1991

Related U.S. Application Data

[63] Continuation of Ser. No. 511,820, Apr. 16, 1990, abandoned, which is a continuation of Ser. No. 161,926, Feb. 29, 1988, abandoned, which is a continuation-in-part of Ser. No. 925,641, Oct. 31, 1986, abandoned.

[51] Int. Cl.$^5$ .................. A61K 31/54; A61K 31/60
[52] U.S. Cl. .................. 514/159; 514/224.2; 514/254; 514/255; 514/356; 514/570; 514/447
[58] Field of Search ............ 514/159, 225, 254, 255, 514/356, 520, 447

[56] References Cited

U.S. PATENT DOCUMENTS

| | | | |
|---|---|---|---|
| 3,591,584 | 7/1971 | Lombardino | 260/243 |
| 3,669,966 | 6/1972 | Ambrogi et al. | 260/250 R |
| 3,892,857 | 7/1975 | Difazio et al. | 424/241 |
| 3,989,816 | 11/1976 | Rajadhyaksha | 424/60 |
| 4,126,681 | 11/1978 | Reller | 424/234 |
| 4,188,390 | 2/1980 | Campbell | 424/251 |
| 4,219,548 | 8/1980 | Reller | 424/234 |
| 4,299,826 | 11/1981 | Luedders | 514/947 |
| 4,309,427 | 1/1982 | Lombardino | 424/246 |
| 4,316,893 | 2/1982 | Rajadhyaksha | 424/180 |
| 4,405,616 | 9/1983 | Rajadhyaksha | 424/244 |
| 4,444,762 | 4/1984 | Rajadhyaksha | 424/180 |
| 4,537,776 | 8/1985 | Cooper | 514/424 |
| 4,552,872 | 11/1985 | Cooper et al. | 514/175 |
| 4,557,934 | 12/1985 | Cooper | 424/128 |
| 4,563,452 | 1/1986 | Soler | 514/222 |
| 4,572,909 | 2/1986 | Campbell et al. | 514/356 |
| 4,626,539 | 12/1986 | Aungst et al. | 514/282 |
| 4,654,209 | 3/1987 | Leslie et al. | 424/80 |
| 4,863,970 | 9/1989 | Patel et al. | 514/784 |

FOREIGN PATENT DOCUMENTS

| | | |
|---|---|---|
| 8319947 | 4/1984 | Australia . |
| 43738 | 1/1982 | European Pat. Off. . |
| 127426 | 12/1984 | European Pat. Off. . |
| 127468 | 12/1984 | European Pat. Off. . |
| 185948 | 4/1980 | New Zealand . |
| 8704706 | 8/1982 | PCT Int'l Appl. . |

OTHER PUBLICATIONS

Stoughton, Enhanced Percutaneous Penetration with 1-Dodecylazacycloheptan-2-one, ARch. Derm., 118, 474-477 (1982).

Cooper, Increased Skin Permeability for Lipophilic Molecules, J. Pharm. Sci., 73, 1153-1156 (1984).

Akhter et al., Penetration Enhancers in Human Skin—Effect of Oleic Acid and Azone on Flurbiprofen Permeation, J. Pharm. Pharmacol., 36, 7P (1984).

Patel et al., Comparative Study of Propylene Glycol and Caprylic/Capric Triglyceride Vehicles for Topical Application, J. Soc. Cosmetic Chem., 36, 303-311 (1985).

Golden et al., Role of Stratum Corneum Lipid Fluidity in Transdermal Drug Flux, J. Pharm. Sci., 76, 25-28 (1987).

Priborsky et al., Combination Effect of Penetration Enhancers and Propylene Glycol on In Vitro Transdermal Absorption of Insulin, Drug Design & Delivery, 2, 91-97 (1987).

Cooper et al., Effect of Fatty Acids and Alcohols on the Penetration of Acyclovir Across Human Skin In Vitro, J. Pharm. Sci., 74, 688-689 (1985).

Bennett et al., Optimization of Bioavailability of Topical Steroids: Non-Occluded Penetration Enhancers Under Thermodynamic Control, J. Pharm. Pharmacol., 37, 298-304 (1985).

Bennett et al., The Assessment of Some Potential Penetration Enhancers Using the Vascoconstrictor Test, J. Pharm. Pharmacol., 36, 8P (1984).

Bennett et al., Effectiveness of Skin Penetration Enhancers Propylene Glycol, Azone, Decylmethylsulphoxide and Oleic Acid with Model Polar (Mannitol) and Nonpolar (Hydrocortisone) Penetrants, J. Pharm. Pharmacol, 37, 84P (1985).

*Primary Examiner*—Leonard Schenkman
*Attorney, Agent, or Firm*—Peter C. Richardson; J. Trevor Lumb; Gregg C. Benson

[57] ABSTRACT

A transdermal flux enhancing pharmaceutical composition for transdermal administration to a human or lower animal subject comprising a safe and effective amount of pharmacologically active compound or a prodrug thereof, an aqueous solvent system comprising from about 15 to 75% by volume of one or more water miscible solvents, and a penetration enhancer selected from certain 1-alkylazacycloheptan-2-ones and cis-olefin compounds of the formula

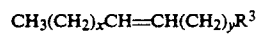

$$CH_3(CH_2)_xCH=CH(CH_2)_yR^3$$

where $R^3$ is $CH_2OH$, $CH_2NH_2$ or $COR^4$ and $R^4$ is OH or ($C_1$-$C_4$)alkoxy, x and y are each an integer from 3 to 13 and the sum of x and y is from 10 to 16; methods for their use in treating various illnesses in a human or lower animal by transdermal administration of said composition.

35 Claims, No Drawings

TRANSDERMAL FLUX ENHANCING COMPOSITIONS

CROSS REFERENCE TO RELATED APPLICATION

This application is a continuation of application Ser. No. 07/511,820, filed Apr. 16, 1990, now abandoned, which is a continuation of application Ser. No. 07/161,926, filed Feb. 29, 1988, now abandoned which is a continuation-in-part of co-pending application Ser. No. 925,641, filed Oct. 31, 1986.

BACKGROUND OF THE INVENTION

The invention relates to flux enhancing pharmaceutical compositions for transdermal administration to a human or lower animal subject and methods for their use in treatment of various illnesses.

DESCRIPTION OF THE PRIOR ART

The following patents to Rajadhyaksha issued from 1976 to 1984 disclose methods and compositions employing 1-alkylazacycloheptan-2-ones and homologs thereof for enhanced penetration of pharmacologically active agents through human and animal skin;

U.S. Pat. Nos. 3,989,816; 4,316,893; 4,405,616 and 4,444,762.

Stoughton, Arch. Derm., 118, 474–477 (1982) relates to 1-dodecylazacycloheptan-2-one, referred to herein as Azone, and its ability to enhance percutaneous penetration.

Cooper, U.S. Pat. Nos. 4,557,934 and 4,537,776, discloses topical compositions of nonsteroidal antiinflammatory compounds, antiviral agents, antitussives and other drugs containing ethanol, certain glycols, pyrrolidone, 1-(2-hydroxyethyl)-aza-cyclopentan-2-one and from 1–35% 1-dodecylazacycloheptan-2-one (Azone).

Cooper, J. Pharm. Sci., 73, 1153–1156 (1984) discloses a method for increased transport of nonpolar molecules like salicylic acid through skin by adding fatty alcohols or fatty acids to transdermal formulations in various glycol solvents.

Akhter and Barry, J. Pharm. Pharmacol., 36, 7P (1984), report that oleic acid and Azone enhance dermal penetration of flurbiprofen formulations in propylene glycol and other solvents.

EP43738 discloses a binary dermal penetration enhancing vehicle for antiinflammatory agents containing a $C_3$–$C_4$-diol, diol ester or diol ether and a cell envelope-disordering compound selected from, inter alia, the lower alkyl esters of $C_{12}$–$C_{14}$ fatty acids, oleic acid, lauryl acetate and myristyl acetate.

Patel, et al., Journ. Soc. Cosmetic Chem. 36, 303–311 (1985) has noted that propylene glycol, a common constituent of prior art pharmaceutical formulations for transdermal use, causes irritation and/or sensitization when its concentration exceeds ten percent.

U.S. Pat. No. 4,572,909, issued Feb. 25, 1986 discloses amlodipine, 2-[(2-aminoethoxy)methyl]-4-(2-chlorophenyl)-3-ethoxycarbonyl-5-methoxycarbonyl -6-methyl-1,4-dihydropyridine and salts thereof, and their use as anti-ischaemic and antihypertensive agents.

U.S. Pat. No. 3,591,584 discloses piroxicam, 4-hydroxy-2-methyl-N-2-pyridinyl-2H-1,2-benzothiazine -3-carboxamide 1,1-dioxide, and its use as an antiinflammatory and analgesic agent.

Pertinent prodrug forms of piroxicam are disclosed in U.S. Pat. Nos. 4,309,427 and 4,563,452.

U.S. Pat. No. 4,188,390 discloses doxazosin, 4-amino-2-[4-(1,4-benzodioxan-2-carbonyl)piperazin -1-yl]-6,7-dimethoxyquinazoline, and its use as a regulator of the cardiovascular system, particularly in treatment of hypertension.

Use of glipizide, 1-cyclohexyl-3-[p-[2-(5-methylpyrazinecarboxamido)ethyl]-phenylsulfonyl]urea, as an antidiabetic agent is disclosed in U.S. Pat. No. 3,669,966.

SUMMARY OF THE INVENTION

The present invention provides novel advantageous transdermal flux enhancing pharmaceutical compositions for transdermal administration to humans or lower animal subjects. The compositions of the invention may incorporate any of a wide variety of pharmacologically active compounds or prodrugs thereof. Thus, the instant compositions comprise a safe and effective amount of a pharmacologically active compound or a prodrug thereof, an aqueous solvent system comprising from about 15 to 75% by volume of one or more water miscible solvents and from about 0.01 to 5% (w/v) of a penetration enhancer selected from a 1-alkylazacycloheptan-2-one wherein said alkyl has from 8 to 16 carbon atoms, and a cis-olefin compound of the formula

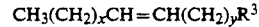

$$CH_3(CH_2)_xCH=CH(CH_2)_yR^3$$

where $R^3$ is $CH_2OH$, $CH_2NH_2$ or $COR^4$ and $R^4$ is OH or $(C_1$–$C_4)$alkoxy, x and y are each an integer from 3 to 13 and the sum of x and y is from 10 to 16. Especially surprising features of the invention are that for a given pharmacologically active compound or prodrug there appears to be a certain concentration of solvent(s) within the above range at which the transdermal flux is optimal and that the solvent system employed must be aqueous. Thus, a particularly preferred composition of the invention is one in which the concentration of the solvent or solvents is within 10% of the concentration which gives optimum transdermal flux for that particular pharmacologically active compound or prodrug. While the entire range of about 15 to 75% for the concentration of the solvent or combined solvents, ordinarily gives markedly improved transdermal flux in comparison with solvent levels outside that range, the more limited range is a "window" within which transdermal flux is found to be most beneficial.

The aqueous solvent system of the invention comprises water and one or more water miscible solvents. Such water miscible solvents include, but are not limited to, methanol, ethanol, isopropyl alcohol, propylene glycol, polyethylene glycol and glycerin. Preferred solvents for this invention are those that are least damaging to skin and include ethanol and glycerin. A particularly preferred solvent of this invention is ethanol. The water used in this invention may be buffered and the pH adjusted to optimize stability of the particular pharmacologically active compound or prodrug and to reduce or eliminate damage to skin. If the water is buffered, it is preferred that the water be buffered to about pH 6.5 to pH 7.5. Anionic buffers are preferable for such purpose. An appropriate pharmaceutically acceptable anionic buffer is Sorensen's Buffer which comprises $NaH_2PO_4.H_2O$, $Na_2HPO_4$ and NaCl and which is well known to those skilled in the art. Certain cationic buffers such as Tris also can be employed but it has been found that Tris reduces the effect of oleic acid on stratum corneum lipids in a concentration dependent manner.

The ratio of water to solvent or solvents for optimum flux will vary to some extent as a function of the solvent(s), penetration enhancer and pharmacologically active compound or prodrug of the particular composition. The range of ratios for water/solvent(s) within the scope of this invention is from about 25/75 (% v/v) to about 85/15 (% v/v).

While the present invention is useful for compositions containing a wide variety of pharmacologically active compounds and prodrugs, it is especially useful for compositions used in treatment of humans or lower animals suffering from rheumatic or inflammatory conditions, ischaemic heart disease, especially angina, hyptertension or diabetes.

Especially useful pharmacologically active compounds or prodrugs for the invention compositions include methyl salicylate, salicylic acid, ibuprofen, piroxicam and prodrugs of piroxicam, and pharmaceutically acceptable cationic and acid addition salts thereof, for treatment of rheumatic or inflammatory conditions. Especially useful prodrugs of piroxicam are those of the formula

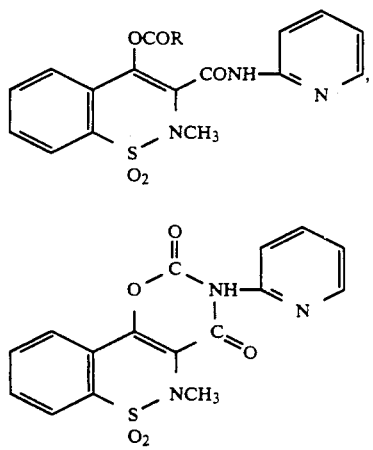

and pharmaceutically acceptable acid addition salts thereof where R is $C_1$ to $C_9$ alkyl, which may be a straight chain or branched alkyl, $CH(R^1)OCOR^2$, where $R^1$ is H or $C_1$ to $C_3$ alkyl and $R^2$ is $C_1$ to $C_4$ alkyl or $C_1$ to $C_4$ alkoxy.

Other preferred compositions of the invention, useful in treating ischaemic heart disease, especially angina, or hypertension in human or lower animals in need of such treatment, are those employing amlodipine, which is disclosed in U.S. Pat. No. 4,572,909, incorporated herein by reference.

Further preferred compositions of the invention are those incorporating a safe and effective amount of glipizide for treatment of diabetic conditions. This pharmacologically active compound and its use for treatment of diabetic conditions is known from U.S. Pat. No. 3,669,966 which is incorporated herein by reference. Yet further preferred compositions of the invention are those employing a safe and effective amount of doxazosin, useful in a preferred method of the invention for treatment of hypertension. The compound and its antihypertensive applications are disclosed in U.S. Pat. No. 4,188,390 which is also incorporated herein by reference.

Ester prodrugs of piroxicam are disclosed in U.S. Pat. No. 4,309,427. U.S. Pat. No. 4,563,452 discloses the above oxazino[5,6-c]1,2-benzothiazine prodrug forms of piroxicam. Each of the two preceding patents are also incorporated herein by reference.

A particularly preferred class of penetration enhancers useful in the invention compositions are the cis-monoenoic acids of the formula

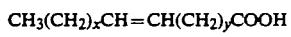

$CH_3(CH_2)_xCH=CH(CH_2)_yCOOH$ wherein x and y are as defined above, and the above 1-alkylazacycloheptan-2-ones wherein said alkyl has from 10 to 14 carbon atoms. Especially preferred members within this class of penetration enhancers are cis-9-tetradecenenoic acid, cis-6-pentadecenoic acid, cis-6-hexadecenoic acid, cis-9-hexadecenoic acid, cis-9-octadecenoic acid (oleic acid), cis-6-octadecenoic acid, cis-11-octadecenoic acid, cis-12-octadecenoic acid, cis-5-eicosenoic, cis-9-eicosenoic acid, cis-11-eicosenoic acid, cis-14-eicosenoic acid, 1-decylazacycloheptan-2-one, 1-dodecylazacycloheptan-2-one and 1-tetradecylazacycloheptan-2-one.

Most particularly preferred penetration enhancers because of their efficacy and ease of availability are cis-9-octadecenoic acid (oleic acid), cis-11-octadecenoic acid (cis-vaccenic acid), and 1-dodecylazacycloheptan-2-one, also referred to herein as Azone.

A preferred range of concentration of water miscible solvent or combined water miscible solvents
for providing optimum transdermal flux of physiologically active compounds and prodrugs thereof in the invention compositions is from 20 to 60% by volume.

A particularly preferred range of concentration for the penetration enhancers of the invention is from 0.1 to 1% w/v and especially from 0.25 to 0.5% w/v for reasons of efficiency and lack of irritation.

As mentioned above, the invention also provides methods of treating rheumatic or inflammatory conditions by employing the pharmaceutical compositions of the invention comprising a safe and effective amount of a pharmacologically active compound selected from methyl salicylate, salicylic acid, ibuprofen, piroxicam and prodrugs of piroxicam.

The invention further provides methods for treatment of ischaemic heart disease or hypertension employing the invention compositions containing a safe and effective amount of amlodipine, a method of treating diabetes employing a safe and effective amount of glipizide and a method for treatment of hypertension employing doxazosin in like manner.

DETAILED DESCRIPTION OF THE INVENTION

A safe and effective amount of a pharmacologically active compound or prodrug for use in the pharmaceutical compositions of the invention is understood herein to mean an amount that will provide therapeutically useful blood and/or local levels of the active compound by the transdermal route of administration. The therapeutically useful levels for the individual pharmacologically active compounds and prodrugs are those known in the art to be useful for each of such compounds. Said pharmaceutical compositions can assume a variety of forms, e.g, a solution, gel or suspension of the active compound or prodrug A prodrug of a physiologically active compound herein means a structurally related compound or derivative of an active compound which is absorbed into the human or lower animal body where it is converted to the desired physiologically active compound. The prodrug itself may have little or none of the desired activity.

Within the scope of sound medical judgment the amount of a given physiologically active compound or prodrug used will vary with the particular condition being treated, the severity of the condition, the duration of the treatment, the nature of the compound employed, the condition of the patient and other factors within the specific knowledge and expertise of the attending physician.

While the pharmaceutical compositions of the invention can employ a wide variety of physiologically active compounds or prodrugs thereof, useful in treatment of, for example, fungal and bacterial infections, inflammatory conditions, pain, ischaemic heart disease including angina pectoris and hypertension, allergic conditions and diabetes, a preferred group of physiologically active compounds includes methyl salicylate, salicylic acid, ibuprofen, piroxicam and the above described prodrugs of piroxicam, all of which are useful in treating rheumatic or inflammatory conditions; amlodipine for treatment of ischaemic heart disease, especially angina, or hypertension; glipizide for treatment of diabetes and doxazosin for treatment of hypertension.

Dosage forms for the pharmaceutical compositions of the invention may include solutions, lotions, ointments, creams, gels, suppositories, rate-limiting sustained release formulations and devices therefor.

In addition to the requisite solvent(s), water and penetration enhancer for the compositions of the invention, typical dosage forms may include inert carriers such as gel-producing materials, mineral oil, emulsifying agents, benzyl alcohol and the like. Specific illustrations of several such formulations are set forth in the examples, below.

The pharmaceutically acceptable salts of the above mentioned physiologically active compounds include both cationic salts of those compounds containing an acidic group such as a carboxylic acid, and acid addition salts of those compounds containing a basic nitrogen atom.

By pharmaceutically acceptable cationic salts is meant the salts formed by neutralization of the free carboxylic acid group of the pharmacologically active compounds e.g, salicylic acid and ibuprofen. The neutralization is brought about by contacting said carboxylic acid containing compounds with a base of a pharmaceutically acceptable metal, ammonia or amine. Examples of such metals are sodium, potassium, calcium and magnesium. Examples of such amines are N-methylglucamine and ethanolamine.

By the term pharmaceutically acceptable acid addition salts is meant those salts formed between the free amino group of the above physiologically active compounds (e.g piroxicam, amlodipine and doxazosin) and a pharmaceutically acceptable acid. Examples of such acids are acetic, benzoic, hydrobromic, hydrochloric, citric, fumaric, maleic, succinic, tartaric, benzenesulfonic, p-toluenesulfonic and methanesulfonic acids.

SKIN SAMPLES FOR PENETRATION STUDIES

Male, hairless mice, 8 to 16 weeks of age, were sacrificed by cervical dislocation. A section of full-thickness abdominal skin was surgically excised and mounted between two identical diffusion half-cells[1] having 1.0 cm$^2$ surface area. The skins were then hydrated for about 18 hours with Sorensen's isotonic buffer (0.067M sodium phosphate, pH 7.38) prior to conducting experiments. Human skin, taken in surgery or autopsy, was dermatoned to about 400 micrometers ($\mu$m) thickness and hydrated in the same manner.

[1] Side-by-side cells obtained from Crown Glass Co., Somerville, New Jersey.

Stratum corneum sheets were prepared from porcine or human skin by trypsin treatment. Thus, full thickness skin samples were dermatomed to a thickness of 350–400 $\mu$m, spread, stratum corneum side up, on filter paper saturated with 0.5% crude trypsin[2] in phosphate buffered saline, pH 7.4. After several hours at 37° C., the stratum corneum layer was peeled away ZO from underlying layers, washed in soybean trypsin inhibitor and several changes of distilled water and spread on wire mesh to dry. Samples were stored desiccated at room temperature until used.

[2] Type II from Sigma Chemical, St. Louis, MO 63178, USA.

EXAMPLE 1

Amlodipine Transdermal Flux Studies

Hairless mouse skin which had been hydrated for 18 hours with Sorensen isotonic buffer (pH 7.38) was mounted in the diffusion cell. The appropriate donor and receiver phases were inserted to replace the hydration solution. Continuous mixing in each half-cell was provided by magnetic stirbars driven by a synchronous motor set at 300 RPM. The diffusion cells were jacketed and maintained at 37° C. with a circulating water manifold system for the entire experiment. At 60 to 90 minute intervals the receiver, containing about 3.0 ml, was removed and assayed by HPLC for amlodipine. The receiver chamber was replenished with fresh solution to replace the material assayed. The amount of amlodipine transported per unit of time was calculated and reported as the steady-state flux.

Amlodipine Donor/Receiver Solutions

Amlodipine benzenesulfonate, 2-[(2-aminoethoxy)-methyl]-4-(2-chlorophenyl)-3-ethoxycarbonyl-5-methoxy carbonyl-6-methyl-1,4-dihydropyridine benzenesulfonate, was used in all studies. Aqueous ethanol solutions containing 55%, 30% and 20% ethanol by volume in 0.01M acetate buffer, pH5, were prepared. To a portion of these solutions was added sufficient cis-9-octadecenoic acid (oleic acid) to give a concentration of 0.25% v/v (0.224% w/v). To other portions Azone was added to a concentration of 0.5% v/v. The solubility of amlodipine benzenesulfonate at 25° C. was determined for each vehicle, such that an 80% saturated drug solution could be employed as the donor phase. The equivalent of the donor solution, without drug or penetration enhancer (cis-9-octadecenoic acid (oleic acid) or Azone) was used in the receiver compartment.

Amlodipine Assay

Analysis of amlodipine was acheived using high performance liquid chromatography (HPLC) with UV detection at 240 nanometers. The mobile phase was 6 mmolar 1-octane sodium sulfonate, 42% (v/v) acetonitrile and 1% (v/v) tetrahydrofuran in a 0.1M sodium dihydrogen orthophosphate buffer adjusted to pH 3.0 with 85% (w/v) orthophosphoric acid. The flow rate was maintained at 1.0 ml/minute at 32° C. All samples and standards were diluted at least 1:1 with mobile phase prior to injection. Peak height calibration curves were linear, with a detection limit of approximately 0.05 μg/ml The results of the study are summarized in the table below.

TABLE

In Vitro Transport of Amlodipine (as the benzenesulfonate) Across Hairless Mouse Skin with Aqueous Ethanol Solvent and Azone≠ or Oleic Acid as Penetration Enhancers

| Amlodipine conc., mg/ml* | Azone≠, % v/v | Oleic, Acid % v/v | Ethanol, % v/v | pH | Flux, mg/day/30 cm$^2$ | Time Lag, Hours | Relative Flux≠≠ |
|---|---|---|---|---|---|---|---|
| 97.2 | 0.5 | — | 55 | 5.2 | 28.5 (13.2)** | 3.2 | 17 |
| 94.0 | — | 0.25 | 55 | 4.9 | 58.0 (13.2) | 4.2 | 34 |
| 97.5 | — | — | 55 | 5.0 | 7.5 (4.5) | 4.1 | 4.4 |
| 10.0 | 0.5 | — | 30 | 5.2 | 148.1 (13.2) | 1.5 | 87 |
| 9.9 | — | 0.25 | 30 | 4.9 | 99.5 (13.4) | 3.4 | 58 |
| 10.3 | — | — | 30 | 5.1 | 1.7 (0.2) | 4.2 | 1.0 |
| 3.6 | 0.5 | — | 20 | 5.4 | 59.2 (13.2) | 1.9 | 35 |
| 3.3 | — | 0.25 | 20 | 4.9 | 37.9 (7.6) | 5.0 | 22 |
| 3.7 | — | — | 20 | 4.9 | 2.2 (1.4) | 3.2 | 1.3 |

*Concentration of amlodipine as the free base.
**Numbers in parentheses are the standard deviation from the mean.
≠Azone is 1-dodecylazacycloheptan-2-one.
≠≠Flux relative to that obtained with 30% v/v ethanol with no penetration enhancer.

Discussion

Maximum flux of amlodipine was achieved with the 30% ethanol vehicle with either Azone or cis-9-octadecenoic acid (oleic acid) as penetration enhancer. This was true in spite of the fact that the 30% ethanol vehicle contained roughly ten times less drug than the 55% ethanol vehicle. The respective flux rates for the azone and cis-9-octadecenoic acid (oleic acid) vehicles containing 30% ethanol were 87 and 58 times, over the same vehicle containing no penetration enhancer. The time to reach steady-state flux, i.e., the lag time, for amlodipine from the cis-9-octadecenoic acid (oleic acid) vehicles ranged from 3.4 to 5.0 hours. The lag time for the azone vehicles was only 1.5 to 3.2 hours. The difference in lag time between the two groups of penetration enhancers was judged to be insignificant.

EXAMPLE 2

Piroxicam Transdermal Flux Studies

The in vitro flux of piroxicam was measured from ethanol/buffer vehicles containing 0.25% v/v (0.224% w/v) cis-9-octadecenoic acid (oleic acid). The buffer employed was Sorensen's Buffer, pH 7.3–7.4[3], all experiments were carried out at 32° C. Samples of either hairless mouse skin or human skin were mounted between two halves of the same diffusion apparatus employed in amlodipine studies. Buffer only was introduced into the chamber (receiver) in contact with the internal side of the skin. The donor chamber, in contact with the outer side of the skin was filled with the appropriate ethanol/buffer vehicle containing 0.25% v/v cis-9-octadecenoic acid (oleic acid) and an excess of piroxicam. The saturation concentration of piroxicam in each of the ethanol/buffer vehicles containing 0.25% v/v cis-9-octadecenoic acid (oleic acid) as calculated by HPLC assay is set forth below.

[3]The buffer was prepared from 3.68 g sodium dihydrogen phosphate monohydrate, 15.15 g disodium hydrogen phosphate, 8.80 g sodium chloride diluted to 2000 ml with deionized water.

| % v/v Ethanol/buffer Containing 0.25% v/v cis-9-octadecenoic (oleic acid) | Saturation Concentration of Piroxicam, mg/ml |
|---|---|
| 0/100 | 0.04 |
| 10/90 | 0.19 |
| 20/80 | 0.46 |
| 30/70 | 0.71 |
| 40/60 | 1.2 |
| 50/50 | 1.5 |
| 100/0 | 1.2 |

The quantity of piroxicam transported across the skin with each vehicle was determined by HPLC assay of samples taken from the receiver periodically over 72 hours. Results obtained with hairless mouse skin and human skin are summmarized in Tablse I and II, below.

TABLE I

Piroxicam Flux Through Hairless Mouse Skin in vitro with various Ethanol/Buffer Vehicles (Each Containing 0.25% v/v Oleic Acid) at 32° C.

| % v/v Ethanol/Buffer | Piroxicam Flux (g/cm$^2$/hr)[a] | Relative Flux[b] |
|---|---|---|
| 0/100 | 0 | — |
| 10/90 | 1.7 | 1.1 |
| 20/80 | 7.7 (1.8) | 5.1 (1.2) |
| 30/70 | 16.0 | 10.7 |
| 40/60 | 24.0 (36) | 16 (24) |
| 50/50 | 20.0 | 13.3 |
| 100/0 | 1.5 | 1.0 |

TABLE II

Piroxicam Flux Through Human Skin in vitro with Various Ethanol/Buffer Vehicles (Each Containing 0.25% v/v Oleic Acid) at 32° C.

| % v/v Ethanol/Buffer | Piroxicam Flux (μg/cm$^2$/hr) | Relative Flux[c] |
|---|---|---|
| 0/100 | .02 | 0.3 |
| 20/80 | 0.18 | 3.0 |
| 40/60 | 0.43 | 7.2 |
| 100/0 | 0.06 | 1.0 |

[c]Flux relative to that with 100% ethanol/0.25% v/v cis-9-octadecenoic acid (oleic acid).

The High Performance Liquid Chromatography (HPLC) assay was carried out using a reverse phase C$_{18}$ μbondapack column (Waters Chromatography, Milton, MA 01757).

Mobile Phase: 40:40:15:15 v/v 0.1M potassium dihydrogen phosphate (pH 3.0), methanol, acetonitrile, tetrahydrofuran; flow rate 1 ml/minute.

Detector: Ultraviolet 313 manometers wavelength LDC/Milton Roy Spectromonitor D.

Injector: Autosample/autoinject, 10 ml injections.

When the above procedure was repeated, but with saturated piroxicam solutions in ethanol, buffer and ethanol/buffer solutions containing 20, 30, 40 and 50% v/v ethanol, and each vehicle containing 0.25% v/v (0.23% w/v) 1-dodecylazacycloheptan-2-one (Azone), the flux rates through hairless mouse skin areas are as set forth in Table III.

TABLE III

Piroxicam Flux Through Hairless Mouse Skin in vitro with Various Ethanol/Buffer Vehicles (Each containing 0.25% Azone) at 32° C.

| % v/v Ethanol/Buffer | Piroxicam Flux ($\mu g/cm^2/hr$) | Relative Flux[d] |
|---|---|---|
| 0/100 | 0.05 | 0.2 |
| 20/80 | 3.7 | 5.3 |
| 30/70 | 11.0 | 15.7 |
| 40/60 | 42.8 | 61 |
| 50/50 | 55.7 | 80 |
| 100/0 | 0.7 | 1 |

[d]Flux relative to that 100% ethanol/0.25% v/v Azone.

EXAMPLE 3

Transdermal Flux of Prodrugs of Piroxicam

Two saturated solutions of 4-n-butyryloxy-2-methyl-N-2-pyridyl-2H-1,2-benzothiazine-3-carboxamide 1,1-dioxide (the n-butyric acid ester of piroxicam) in Ethanol/45 Sorensen's pH 7.3 buffer, by volume, were prepared. One of the solutions was adjusted with cis-9-octadecenoic acid (oleic acid) to 0.224% w/v (0.25% v/v). The flux rate through hairless mouse skin was measured for the two solutions by HPLC assay for piroxicam in the receiver cell by the same method employed above for piroxicam. The results are summarized below.

In Vitro Flux Through Hairless Mouse Skin of 55/45 v/v Ethanol/Buffer Vehicle With and Without Oleic Acid, at 32° C.

| % Oleic Acid | Piroxicam Flux ($\mu g/cm^2/hr$) | Relative Flux |
|---|---|---|
| 0.224 w/v | 4.10 ± 0.40 | 24 |
| None | 0.17 ± 0.02 | 1 |

When 4-n-pentanoyloxy-2-methyl-N-2-pyridyl-2H-1,2-benzothiazine-3-carboxamide 1,1-dioxide was emplyed in place of the above n-butyrate ester of piroxicam in the above procedure, the results obtained were as follows:

| % Oleic Acid | Piroxicam Flux ($\mu g/cm^2/hr$) | Relative Flux |
|---|---|---|
| 0.224 w/v | 7.93 ± 0.62 | 14 |
| None | 0.56 ± 0.17 | 1 |

EXAMPLE 4

Correlation of Effects of Various Fatty Acids on Flux Enhancement of Salicylic Acid, Infrared Spectral Data and Differential Scanning Calorimetry with Porcine Stratum Corneum Stratum corneum sheets were prepared from porcine skin by trypsin treatment. Thus, full thickness porcine skin samples were dermatomed to 350 $\mu$m thickness and spread, stratum corneum side up, on filter paper saturated with 0.5% crude trypsin in phosphate buffered saline at pH 7.4 (Sorensen's buffer). After several hours at 37° C. the stratum corneum was peeled away, washed in soybean trypsin inhibitor, water and air dried. Samples were stored desiccated at room temperature until used. Prior to use, dry skin samples of known weight were incubated for two hours in an 0.15M solution of the appropriate fatty acid in ethanol, the samples were then washed for ten seconds in ethanol, spread on wire mesh, dried over a desiccant and the dry sample reweighed. The stratum corneum samples were then held for several days in a chamber at 22° C., 95% relative humidity, during which the stratum corneum samples equilibrated to a water content of 30% (w/w).

Infrared Spectral Data

Infrared spectra were obtained with a Fourier Transform Infrared Spectrometer[4] (FTIR) equipped with a liquid nitrogen cooled mercury-cadmium telluride detector. In order to prevent water loss, hydrated samples were sealed between zinc sulfide windows while maintained at 22° C., 95% relative humidity. Sealed samples were placed in the spectrometer where an average of 127 scans were obtained in about six minutes for each of the fatty acid treatments. The digitized data were transferred to a computer (Apple IIe) for determination of frequency and bandwidth of the C—H antisymmetric stretching absorbance. Due to the digital nature of the FTIR instrument, absorbance and frequency data exist only in discrete increments. With the instrument used, the exact value of any frequency point could only be determined with a precision not greater than 2.7 cm$^{-1}$. The peak frequency was estimated with much greater precision, however, using a center of gravity algorithm for digitized data reported by Cameron et al., Applied Spectr., 36 245–250 (1982).

[4]Analect model FX-6200, Laser Precision Corp., Irvine, California.

Differential Scanninq Calorimetry (DSC)

The differential scanning calorimeter[5] was used at a scan rate of 0.75° C./minute. Duplicate samples from each of the above FTIR experiments were combined for DSC measurements. Alternately, stratum corneum samples of known weight (about 20 mg) were treated with each fatty acid in the same manner described above. Treated samples were hydrated for several days at 95% R.H., 22° C. and reweighed. Results show approximately 30% (w/w) water uptake regardless of fatty acid employed.

[5]Microcal model MC-1, Microcal Inc., Amherst, Massachusetts.

Flux Method

Sheets of excised porcine skin cut to 350 $\mu$m thickness were mounted between two halves of a diffusion cell with the stratum corneum side toward the donor compartment which contained 1.0 ml of saturated salicylic acid in ethanol (0.31 grams/ml) plus about $10^5 dpm^6$/ml of $^{14}$C-labeled salicylic acid. The appropriate fatty acid was then added to give a final concentration of 0.15M. The receiver compartment contained 1.0 ml Sorensen's buffer, pH 7.4. Both compartments were stirred with a magnetic stirrer and maintained at 32° C.

$^6$dpm=disintegration minute, $$dpm = \frac{\text{photons counts per minute}}{\text{efficiency of the counting}}$$

Samples were removed periodically from the receiver side of the diffusion cell, mixed with a Z0 scintillation cocktail (Scintisol, Isolabs, Inc., Akron, OH) and counted for several minutes in a liquid scintillation counter (Model Mark III-6881, Tracor Analytical, Elk Grove Village, IL). Following an initial lag time of about 6 hours, the amount of salicylic acid appearing in the receiver side was linear with time for the duration of the experiment (routinely 24 to 48 hours). From a linear least squares analysis of these data the rate of appearance of salicylic acid in the receiver (dpm/hr.) was determined. This value, when divided by the specific acitivity of salicyclic acid in the saturated solution (approximately 300 dpm/mg) and the area of exposed skin (0.2 cm$^2$), yielded the flux (mg/cm$^2$/hr). Samples removed from the donor side at the beginning and end of the experiment contained, within error, the same amount of salicylic acid. Thus, constant concentration of the permeant was maintained on the donor side throughout the experiment.

The results of all three studies are summarized in Table IV.

TABLE IV

A summary of spectral, thermal and flux changes following treatment of porcine stratum corneum with fatty acids of 18 carbon length. The IR and DSC results were obtained with samples hydrated to 30% (w/w) water content. For the monounsaturated acids, the form (cis vs. trans) and position along the carbon chain of each isomer is shown in parentheses. Each value represents the average of at least two samples.

| Treatment | Peak IR Frequency (cm$^{-1}$) | DSC T$_m$≠ (°C.) | Flux of Salicyclic Acid (mg/cm$^2$/hr) |
|---|---|---|---|
| Stearic | *2918.0 ± 0.4 | *62.5 ± 1.0 | 1.21 |
| Petroselenic (cis-6,7) | 2919.0 | 60.5 | 0.79 |
| Petroseladic (trans-6,7) | 2919.0 | 62.0 | 0.97 |
| Oleic (cis-9,10) | *2920.0 ± 0.5 | *59.0 ± 1.5 | 3.81 |
| Elaidic (trans-9,10) | 2919.4 | 61.5 | 2.35 |
| cis-vaccenic (cis-11,12) | 2920.1 | 57.0 | 5.53 |
| trans-vaccenic (trans-11,12) | 2818.8 | 61.0 | 1.11 |
| Ethanol | *2918.8 ± 0.4 | *62.0 ± 1.0 | 1.31 |
| No Treatment | 2918.8 | 62.0 | — |

*Value represents the average ± SEM of three samples.
≠Temperature of the transition maximum.

Oleic and cis-vaccenic acids each gave a maximum infrared absorbance at 2920 cm$^{-1}$ while the saturated stearic acid and the two trans-acids gave lower values (about 2918–2919), as did the controls. While the differences between the groups of fatty acids is less than the digital resolution of the instrument (2.7 cm$^{-1}$, the center of gravity technique of peak frequency determination allows sufficient precision to easily estimate differences of less than 1.0 cm$^{-1}$ from digitized data. Furthermore, several of the experiments were repeated in triplicate with a standard error of the mean of less than 0.5 cm$^{-1}$. Thus, while small, the peak frequency changes following treatment of stratum corneum with oleic and cis-vaccenic acid compared to the others, are significant.

From the DSC data it is also seen that the two cis-fatty acids show decreased temperature of the transition maxima when compared to stearic acid, the two trans-fatty acids and the controls. It was also noted that the cis-fatty acids gave a broader peak (ratio of peak width to peak height) than did others. The data also suggests that increasing the distance of the double bond from the carboxyl group gives rise to a larger decrease in Tm.

The flux data for cis-9-octadecenoic acid (oleic acid) is also significantly greater than that of stearic acid, the ethanol control and elaidic acid. The difference in flux rates is even greater for cis-vaccenic acid relative to the controls and trans-vaccenic acid. Thus, the above infrared and DSC results each show a high degree of correlation with flux rate.

EXAMPLE 5

Correlation of Lipid Melting Temperature by DSC with Ethanol Concentration of Aqueous Vehicles Containing Oleic Acid Employing the above procedure for obtaining lipid transition temperature of procein stratum corneum samples by differential scanning calorimetry, the melting temperature, Tm, foe stratum corneum in various ethanol/Sorensen's buffer solutions, each containing 0.25% v/v cis-9-octadecenoic acid (oleic acid) (0.22 w/v), were obtained. The results are summarized in the following table.

| % Ethanol (v/v) in Ethanol/Buffer Vehicles Containing 0.25% v/v Oleic Acid | Porcine Stratum Corneum Lipid Transition Temperature, Tm, °C. |
|---|---|
| 0/100 | 57.5 |
| 20/80 | 54.5 |
| 30/70 | 54.0 |
| 40/60 | 53.2 ± 0.6 |
| 50/50 | 55.1 |
| 60/40 | 53.4 |
| 70/30 | 58.8 |
| 100/0 | 66.4 |

*Sorensen's Buffer, pH 7.3.
Under the same conditions, stratum corneum samples in Sorensen's buffer alone (no ethanol or cis-9-octadecenoic acid (oleic acid)) gave a Tm of 64° C. Stratum corneum in a vehicle containing 40/60 v/v ethanol/buffer with no cis-9-octadecenoic acid (oleic acid) also had a Tm of 64° C.
The above results, strongly suggest that the 20–70% v/v ethanol vehicles, and especially those having 30–60% ethanol, have a unique ability to disrupt the stratum corneum, a property which is indicative of enhancement of transdermal flux.

EXAMPLE 6

Employing the procedure of Example 2, but employing saturated solutions of methyl salicylate and ibuprofen, 2-(4-isobutylphenyl)propionic acid, in place of piroxicam, in ethanol/Sorensen's buffer solutions, each containing 0.25% v/v cis-9-octadecenoic acid (oleic acid), gave the following relative flux results through hairless mouse skin.

Relative Flux of Methyl Salicylate Through
Hairless Mouse Skin from Ethanol/Buffer Vehicles
Containing 0.25% v/v Oleic Acid

| % Ethanol/Buffer, v/v | Relative Flux* |
|---|---|
| 0/100 | 1 |
| 20/80 | 6 |
| 30/70 | 11.5 |
| 40/60 | 80 |
| 50/50 | 200 |
| .60/40 | 450 |
| 70/30 | 300 |
| 100/0 | 4 (estimated) |

*Flux relative to that with 0/100 ethanol/buffer.

Relative Flux of Ibuprofen Through Hairless
Mouse Skin from Ethanol/Buffer Vehicles
Containing 0.25% v/v Oleic Acid

| % Ethanol/Buffer v/v | Relative Flux* |
|---|---|
| 0/100 | 1.0 |
| 20/80 | 1.5 |
| 30/70 | 1.8 |
| 40/60 | 3.5 |
| 50/50 | 5 |
| 60/40 | 4.5 |
| 70/30 | 4.5 |
| 100/0 | 4.5 |

*Flux relative to that with 0/100 ethanol/buffer.

EXAMPLE 7

Transdermal Flux of Doxazosin Through Hairless Mouse Skin

Donor solutions were prepared by dissolving doxazosin free base in a 30 v/v ethanol/buffer (0.1M sodium acetate, pH 5) containing 0.5% v/v 1-dodecylazacycloheptan-2-one (Azone) and a specified amount of methanesulfonic acid (mesylate). Four different doxazosin concentrations ranging from 2.2 to 8.95 mg/ml were employed in vehicles containing ether 1.3 or 2.2 mg/ml mesylate. A control with no Azone was included at the highest donor concentration. Receiver solutions contained 30% v/v ethanol/buffer only.

Analysis of doxazosin was accomplished using high pressure liquid chromatography, with UV detection at 246 nm. The mobile phase consisted of 6 mM 1-octane sodium sulphonate, 35% (v/v) acetonitrile and 1% (v/v) tetrahydrofuran in a 0.1M sodium dihydrogen orthophosphate buffer. The final pH was adjusted to 3.0 with 85% (w/v) orthophosphoric acid. During the analysis, the flow rate was maintained at 1.3 ml/minute through a Waters Nova-Pak (15 cm, 3 μm particles) C18 column, thermostated at 38° C. All samples (and standards) were diluted at least 1:1 with mobile phase prior to injection. Peak height calibration curves were linear, with a detection limit of approximately 0.05 μg/ml As in the following experiments with glipizide, flux rates were calculated from the HPLC data. The results are summarized in the table.

In Vitro Transport of Doxazosin Across Hairless Mouse
Skin Employing the Soluble Mesylate Salt in Vehicles
Containing 30% Ethanol and ½% Azone

| Concentration | | | | Flux$^c$ | |
|---|---|---|---|---|---|
| Cdonor$^a$ (mg/ml) | Mesylate (mg/ml) | Azone$^d$ % v/v | pH$^b$ | (mg/day/ 30 cm$^2$) | Lag Time (hours) |
| 8.95 | 2.2 | 0.5 | 4.3 | 59.4 (7.5) | 2.1 |
| 8.55 | 2.2 | — | 4.2 | 0.6 (0.1) | <1.5 |
| 4.31 | 2.2 | 0.5 | 4.8 | 32.1 (15.2) | 2.5 |
| 6.82 | 1.3 | 0.5 | 4.6 | 42.3 (9.7) | 1.8 |
| 4.35 | 1.3 | 0.5 | 4.8 | 30.2 (4.4) | 1.5 |
| 4.24 | 1.3 | 0.5 | 4.9 | 28.7 | 1.8 |
| 2.24 | 1.3 | 0.5 | 5.1 | 12.2 (5.6) | 1.6 |
| 2.21 | 1.3 | 0.5 | 5.0 | 13.8 (6.4) | 2.5 |

$^a$Concentration of doxazosin as the free base.
$^b$Final pH of the donor phase (initial pH was 5.0 in all cases).
$^c$Numbers in parentheses refer to the standard deviation of the mean.
$^d$0.5% v/v corresponds to 0.46% w/v.

Discussion

The in vitro flux ranged from 12 to 59 mg/day/30 cm$^2$, depending on the particular donor concentration of doxazosin. The relationship between flux and donor concentration was apparently linear and independent of mesylate. The highest concentration tested (i.e., 8.95 mg/ml) represents the saturation solubility of doxazosin mesylate in 30% ethanol/buffer (0.1M acetate, pH 5) and limiting transport rate at 25° C. The control (no Azone) donor vehicle yielded a flux of 0.6 mg/day/30 cm$^2$, roughly 100× less than the corresponding vehicle with Azone.

Under the same conditions as above a donor solution of 2.40 mg/ml doxazosin free base (no mesylylate) in 55% v/v ethanol/buffer containing 3% v/v Azone gave a flux of 46.2 mg/day/30 cm$^2$.

EXAMPLE 8

Transdermal Flux of Glipizide Through Hairless Mouse Skin

The transdermal flux of glipizide, 1-cyclohexyl-3-[[p-[2-(5-methylpyrazinecarboxamido)ethyl]phenyl]-sulfonyl]]urea, solutions in 20, 30 and 55% ethanol (v/v) employing Azone, N-dodecyl-1-azacycloheptan-2-one, as penetrant enhancer. Each vehicle was tested with and without 0.5% v/v Azone7 at a pH of about 9 in 0.01M TRIS buffer. The equivalent of the donor solution without glipizide or Azone was used in the receiver compartment.

[7]The density of Azone at 25° C. is 0.912 g/ml Thus, the Azone solutions are each 0.46% w/v.

Analysis of glipizide was achieved using HPLC with a 228 nm Ultraviolet detector. The mobile phase consisted of 41% v/v acetonitrile in 0.1M sodium dihydrogen phosphate buffer. The final pH was adjusted to 4.0 with 85% w/v phosphoric acid. The flow rate of the mobile phase was maintained at 1.0 ml/minute through a Waters Novapak column (15 cm. with 3 μm particle size) at 32° C. All samples were diluted at least 1:1 with mobile phase prior to injection. Peak height calibration curves were linear, detection limit about 0.05 μg/ml From the results of the HPLC analysis, the amount of glipizide transported through hairless mouse skin per unit time was calculated and reported as steady-state flux. The results are summarized in the table below.

In Vitro Transport of Glipizide Across Hairless Mouse Skin

| Glipizide (mg/ml) | Azone (% v/v) | EtOH (% v/v) | pH | Flux[a] (mg/day/ 30 cm$^2$) | Time Lag (hr) |
|---|---|---|---|---|---|
| 17.5 | 0.5 | 55 | 8.8 | 30.8 (6.5) | 3.6 |
| 17.9 | — | 55 | 9.1 | 2.7 (0.5) | 4.6 |
| 8.1 | 0.5 | 30 | 8.8 | 101.4 (10.3) | 1.7 |
| 8.2 | — | 30 | 8.9 | 0.6 (0.2) | 0.4 |
| 6.8 | 0.5 | 20 | 8.8 | 55.9 (38.8) | 3.3 |
| 6.7 | — | 20 | 8.9 | 0.4 (0.04) | 0.5 |

[a]Numbers in parentheses refer to the standard deviation of the mean.

Discussion

The in vitro transport of glipizide across hairless mouse skin ranged from 30.8 to 101.4 mg/day/30 cm$^2$. Increasing the concentration of the drug did not necessarily result in an increase flux. The highest flux was observed in 30% ethanol containing 0.5% v/v Azone. Although the drug concentration in this vehicle was only half that of the 55% ethanol vehicle, the transport rate was approximately 3.5 times greater. Similar behavior was noted in Example 1 with amlodipine.

EXAMPLE 9

Solution formulations are prepared as follows:

A. Oleic Acid 0.25 g or Azone 0.50 g
   Amlodipine benzenesulfonate 1.0 g
   Ethanol 30.0 ml
   Water q.s. to make 100 ml
   Adjust to pH 5.0 with sodium hydroxide
B. Oleic acid 0.25 g or Azone 0.50 g
   Doxazosin mesylate 0.90 g
   ethanol 30.0 ml
   Water q.s. to make 100 ml
   NaOH q.s. to adjust to pH 5.0.
C. Oleic acid 0.25 g or Azone 0.50 g or
   cis-11-octadecenoic acid 0.75 g
   Piroxicam 1.0 g
   Ethanol 40.0 ml
   Water q.s. to make 100 ml
D. Oleic acid 0.25 g or Azone 0.50 g
   Glipizide 0.80 g
   Ethanol 30.0
   Water q.s. to 100 ml
   NaOH q.s. to pH 9
E. cis-9-tetradecenoic acid 2.0 g
   cis-6-pentadecenoic acid 5.0 g
   cis-6-hexadecenoic acid 1.5 g or
   cis-9-hexadecenoic acid 0.1 g
   Active ingredient 1.0–3.0 g
   Ethanol 15–75 ml
   Water q.s to make 100 ml
F. Oleic acid 0.25 g
   Amlodipine benzensulfonate 1.0 g
   Propylene glycol 40.0 ml
   Water q.s. to 100 ml
   NaOH q.s. to adjust to pH 5.0
G. Oleic acid 0.25 g
   Piroxicam 1.0 g
   Glycerin 40.0 ml
   Water q.s. to 100 ml
   NaOH q.s. to adjust to pH 7.5
H. Azone 0.25 g
   Piroxicam 1.0 g
   Ethanol 40.0 ml
   Water q.s. to 100 ml
   NaOH q.s. to adjust to pH 7.5
I. Oleic acid 0.25 g
   Piroxicam 1.0 g
   Ethanol 20.0 ml
   Propylene glycol 40.0 ml
   Water q.s. to 100 ml
   NaOH q.s. to adjust to pH 7.5
J. Oleic acid 0.5 g
   Piroxicam 1.0 g
   Ethanol 20.0 ml
   Glycerin 40.0 ml
   Water q.s. to 100 ml
   NaOH q.s. to adjust to pH 7.5
K. Oleic acid 0.25 g
   Piroxicam 1.0 g
   Ethanol 20.0 ml
   Propylene glycol 40.0 ml
   Phosphoric acid 0.1 ml
   Water q.s. to 100 ml
   NaOH q.s. to adjust to pH 7.5

EXAMPLE 10

The following are illustrative formulations for gels of the invention compositions.

A. Oleic acid 0.25 g or Azone 0.50 g
   Carbopol 940[8] 0.7 g
   Benzyl alcohol 1.0 g
   Diisopropanolamine 1.1 g
   Hydroxyethylcellulose 0.4 g
   piroxicam 1.0 g
   Ethanol 30.0 ml
   Water q.s. to make 100 ml

[8]Carbopol 940 is a polyacrylic acid polymer available from B. F. Goodrich Co., Inc.

The ingredients are combined, warmed while stirring to effect dispersion and allowed to cool to room temperature.

B. Oleic acid 0.25 g or Azone 0.50 g
   Carbopol 940 0.7 g
   Benzyl alcohol 1.0 g
   Diisopropanolamine 1.1 g
   Hydroxyethylcellulose 0.4 g
   Amlodipine benzenesulfonate 1.0 g
   Ethanol 35 ml
   Water q.s. to make 100 ml The ingredients were treated as in A, above to form the desired gel.

When 0.8 g of glipizide or 1.0 g ibuprofen, 3.0 g salicylic acid 0.9 g of doxazosin mesylate are used in place of amlodipine benzenesulfonate in the above formulation satisfactory gels are obtained in like manner.

C. Penetration enhancer[9] 0.01 to 5.0 g
   Carbopol 940 1.0 g
   Benzyl alcohol 1.0 g
   Diisopropanolamine 1.0 g
   Hydroxyethylcellulose 0.5 g
   One or more watr miscible solvents[10] 15 to 75 ml
   Methyl salicylate 10 g
   Water q.s. to make 100 ml
D. Oleic acid 0.25 g
   Carbopol 940 0.70 g
   Benzyl alcohol 1.0 g
   Diisopropanolamine 1.0 g
   Hydroxyethylcellulose 0.4 g
   Piroxicam 0.5 g
   Ethanol 25.0 ml
   Propylene glycol 20.0 ml -continued

| | |
|---|---|
| Water q.s. to 100 ml | |

[9] Penetration enhancers include cis-9-octadecenoic acid (oleic acid), cis-6-octadecenoic, cis-11-octadecenoic, cis-12-octa-decenoic, cis-5-eicosenoic,, cis-9-eicosenoic, cis-11-eicosenoic and cis-14-eicosenoic acids; 1-decylazacycloheptan-2-one, 1-dodecylazacycloheptan-2-one and 1-tetradecyl-azacycloheptan-2-one, cis-9-octadecenylamine, cis-11-octadecenylamine, cis-14-eicosenylamine, cis-9-tetradecenyl alcohol, cis-11-octadecenyl alcohol, ethyl oleate, ethyl cis-5-eicosenoate, methyl cis-12-octadecenoate, isopropyl cis-9-hexadecenoate and n-butyl cis-9-tetradecenoate.
[10] Water miscible solvents include methanol, ethanol isopropyl alcohol, propylene glycol, polyethylene glycol and glycerin.

The ingredients are treated as in A, above, to form the desired gel.

| E. | Oleic acid | 0.25 g |
|---|---|---|
| | Carbopol 934 | 0.70 g |
| | Benzylalcohol | 1.0 g |
| | Triethanolamine | 1.1 g |
| | Hydroxyethylcellulose | 0.4 g |
| | Piroxicam | 1.0 g |
| | Glycerin | 30.0 ml |
| | Water q.s. to 100 ml. | |

The ingredients are treated as in above A, above, to form the desired gel.

EXAMPLE 11

The following formulations are illustrative of hydrophilic ointments as dosage forms of the compositions of the invention.

| A. | Oleic acid 0.25 g or Azone 0.50 g | |
|---|---|---|
| | PEG 4000[11] | 17.2 g |
| | PEG 400[11] | 17.2 g |
| | Piroxicam-4-(1-ethoxycarbonylethyl)-carbonyl ester prodrug | 1.2 g |
| | Ethanol | 30 ml |
| | Water q.s. to make 100 ml | |
| B | Oleic acid | 0.25 g |
| | active ingredient[12] | 1-5 g |
| | PEG 4000 | 17.0 g |
| | PEG 400 | 17.0 g |
| | One or more water miscible solvents[13] | 15-55 ml |
| | Water q.s. to make | 100 ml |
| C. | Oleic acid | 0.25 g |
| | Piroxicam | 1.0 g |
| | PEG 4000 | 17.2 g |
| | PEG 200[1] | 17.2 g |
| | Propylene glycol | 30.0 ml |
| | Water q.s. to make | 100 ml |
| D. | Oleic acid 0.25 g or Azone | 0.5 g |
| | Piroxicam | 1.0 g |
| | PEG 4000 | 17.2 g |
| | PEG 200 | 17.2 g |
| | Ethanol | 30.0 ml |
| | Water q.s. to make 100 ml | |

[11] PEG 200 is commercial polyethylene glycol of molecular weight 190-210. PEG 400 is commercial polyethylene glycol of molecular weight 380-420. PEG 4000 is commercial polyethylene glycol, M.W. 3000-3700.
[12] Active ingredients include methyl salicylate, salicylic acid, ibuprofen, piroxicam, amlodipine benzenesulfonate, doxazosin mesylate and glipizide.
[13] Water miscible solvents include methanol, ethanol isopropyl alcohol, propylene glycol, polyethylene glycol and glycerin.

EXAMPLE 12

Correlation of Lipid Melting Temperature by DSC with Glycerin Concentration of Aqueous Vehicles Containing Oleic Acid Employing the procedure of Example 4, above, for obtaining lipid transition temperature of porcine stratum corneum samples by differential scanning calorimetry, the melting temperature, Tm, for stratum corneum in various glycerin/0.1M Tris buffer solutions (Ph 6.8-7.3) each containing 0.25% v/v cis-9-octadecenoic acid (oleic acid) (0.22 w/v), were obtained. The results are summarized in the following table.

| % Glycerin (v/v) in 0.1M Tris Buffer (pH 6.8-7.3) Vehicles Containing 0.25% v/v Oleic Acid | Porcine Stratum Corneum Lipid Transition Temperature, Tm, °C. |
|---|---|
| 0/100 | 58 |
| 20/80 | 62.5 |
| 40/60 | 57 |
| 60/40 | 54 |
| 80/20 | 59 |

Under the same conditions, stratum corneum samples in 0.1M Tris buffer (pH 6.8-7.3) alone (no glycerin or cis-9-octadecenoic acid (oleic acid)) gave a Tm of 61° C.

The above results demonstrate that those vehicles having about 40-60% glycerin have the ability to disrupt the stratum corneum, a property which, as discussed in Example 5, is indicative of enhancement of transdermal flux.

EXAMPLE 13

Correlation of Lipid Melting Temperature by DSC with Ethanol Concentration of Aqueous Vehicles Containing Oleic Acid and Tris Buffer Employing the procedure of Example 4, above, for obtaining lipid transition temperature of porcine stratum corneum samples by differential scanning calorimetry, the melting temperature, Tm, for stratum corneum in various ethanol/0.1M Tris buffer solutions (pH 6.8-7.3) each containing 0.25% v/v cis-9-octadecenoic acid (oleic acid) (0.22 w/v) were obtained. The results are summarized in the following table.

| % Ethanol (v/v) in 0.1M Tris Buffer (pH 6.8-7.3) Vehicles Containing 0.25% v/v Oleic Acid | Porcine Stratum Corneum Lipid Transition Temperature, Tm, °C. |
|---|---|
| 0/100 | 58 |
| 20/80 | 59 |
| 40/60 | 55 |
| 60/40 | 59 |
| 80/20 | 61 |

Under the same conditions, stratum corneum samples in 0.1M Tris buffer (pH 6.8-7.3) alone (no ethanol or cis-9-octadecenoic acid (oleic acid)) gave a Tm of 61° C.

The above results when compared to those obtained in Example 5 demonstrate that while the above ethanol vehicles comprising about 40% ethanol in 0.1M Tris buffer (pH 6.8-7.3), disrupt the stratum corneum, the effect is somewhat diminished when compared to similar vehicles in Sorensen's buffer (Example 5).

EXAMPLE 14

Correlation of Lipid Melting Temperature by DSC with Polyethylene Glycol 200 (PEG 200) Concentration of Aqueous Vehicles Containing Oleic Acid Employing the procedure of Example 4, above, for obtaining lipid transition temperature of porcine stratum corneum samples by differential scanning calorimetry, the melting temperature, Tm, for stratum corneum in various PEG 200/0.1M Tris buffer solutions (pH 6.8–7.3) each containing 0.25% v/v cis-9-octadecenoic acid (oleic acid) (0.22 w/v) were obtained. The results are summarized in the following table.

| % PEG 200 (v/v) in 0.1M Tris Buffer (pH 6.8–7.3) Vehicles Containing 0.25% v/v Oleic Acid | Porcine Stratum Corneum Lipid Transition Temperature, Tm, °C. |
| --- | --- |
| 0/100 | 59 |
| 20/80 | 59 |
| 40/60 | 57.5 |
| 60/40 | 57 |
| 80/20 | 61 |

Under the same conditions, stratum corneum samples in 0.1M Tris buffer (pH 6.8–7.3) alone (no PEG 200 or cis-9-octadecenoic acid (oleic acid)) gave a Tm of 61° C.

The above results demonstrate that those vehicles having about 40–60% PEG 200 have the ability to disrupt the stratum corneum, a property which, as discussed in Example 5, is indicative of enhancement of transdermal flux.

EXAMPLE 15

Correlation of Lipid Melting Temperature by DSC with Ethanol and Propylene Glycol (PG) Concentrations of Aqueous Vehicles Containing Oleic Acid Employing the procedure of Example 4, above, for obtaining lipid transition temperature of porcine stratum corneum samples by differential scanning calorimetry, the melting temperature, Tm, for stratum corneum in various ethanol/PG/0.1M Tris buffer solutions (pH 6.8–7.3) each containing 0.25% v/v cis-9-octadecenoic acid (oleic acid) (0.22 w/v) were obtained. The results are summarized in the following table.

| % Ethanol and PG (v/v/v) in 0.1M Tris Buffer (pH 6.8–7.3) Vehicles Containing 0.25% v/v Oleic Acid | Porcine Stratum Corneum Lipid Transition Temperature, Tm, °C. |
| --- | --- |
| 40/20/40 | 58.5 |
| 33/33/34 | 59 |
| 66/34/0 | 60 |
| 20/40/40 | 55 |
| 40/40/20 | 60 |
| 34/66/0 | 61 |

Under the same conditions, stratum corneum samples in 0.1M Tris buffer (pH 6.8–7.3) alone (no ethanol or PG or cis-9-octadecenoic acid (oleic acid)) gave a Tm of 62.5° C.

The above results demonstrate aqueous vehicles having two miscible solvents have the ability to disrupt the stratum corneum and that the degree of disruption can vary with the ratio of the solvents to each other (compare 40/20/40 with a Tm of 58.5° C. to 20/40/40 with a Tm of 55° C.)

EXAMPLE 16

The following formulations are illustrative of creams/lotions as dosage forms of the compositions of this invention.

| | | |
| --- | --- | --- |
| A. | Oleic acid | 0.1 g |
| | Piroxicam | 0.1 g |
| | Sodium lauryl sulfate | 1.0 ml |
| | Ethanol | 30.0 ml |
| | Cetyl alcohol | 15.0 ml |
| | Water q.s. to 100 ml | |
| B. | Oleic Acid | 1.0 g |
| | Carbopol 943 (2% aqueous solution) | 10.0 ml |
| | Liquid paraffin (70) | 25.0 ml |
| | Jojoba wax | 10.0 g |
| | Ceresin | 2.0 g |
| | Beeswax | 8.0 g |
| | Glipizide | 1.0 g |
| | Monoethanolamine | 0.5 g |
| | Glyceryl stearate | 3.5 g |
| | Ethanol | 30.0 ml |
| | Water q.s. to 100 ml. | |

We claim:
1. A transdermal flux enhancing pharmaceutical composition for transdermal administration to a human or lower animal subject comprising
   (a) a safe and effective amount of a pharmacologically active compound or a prodrug thereof,
   (b) an aqueous solvent system comprising from about 30 to 75% by volume of one or more water miscible solvents, and
   (c) from about 0.01 to 5% (w/v) of a penetration enhancer selected from a 1-alkylazacycloheptan-2-one, said alkyl having from 8 to 16 carbon atoms, and a cis-olefin compound of the formula

$$CH_3(CH_2)_xCH=CH(CH_2)_yR^3$$

where $R^3$ is $CH_2OH$, $CH_2NH_2$ or $COR^4$, and $R^4$ is OH or $(C_1-C_4)$alkoxy, x and y are each an integer from 3 to 13 and the sum of x and y is from 10 to 16;
   wherein in (b) the solvent or combined solvents content is from about 30 to 75% by volume and is within 10% of that which gives optimum transdermal flux for said compound or prodrug.

2. The composition according to claim 1 wherein in (c) the penetration enhancer is a cis-monoenoic acid of the formula $$CH_3(CH_2)_xCH=CH(CH_2)_yCOOH$$

wherein x and y are as previously defined, or a 1-alkylazacycloheptan-2-one, said alkyl having from 10 to 14 carbon atoms.

3. The composition according to claim 2 wherein in (c) the penetration enhancer is cis-9-tetradecenoic acid, cis-6-pentadecenoic acid, cis-6-hexadecenoic acid, cis-9-hexadecenoic acid, cis-9-octadecenoic acid (oleic acid), cis-6-octadecenoic acid, cis-11-octadecenoic acid, cis-12-octadecenoic acid, cis-5-eicosenoic, cis-9-eicosenoic acid, cis-11-eicosenoic acid, cis-14-eicosenoic acid, 1-decylazacycloheptan-2-one, 1-dodecylazacycloheptan-2-one or 1-tetradecylazacycloheptan-2-one.

4. The composition according to claim 3 wherein the penetration enhancer is cis-9-octadecenoic acid (oleic acid), cis-11-octadecenoic acid or 1-dodecylazacycloheptan-2-one.

5. The composition according to claim 1 wherein in (b) the water miscible solvents are selected from the group consisting of methanol, ethanol, isopropyl, alcohol, propylene glycol, polyethylene glycol and glycerin.

6. The composition according to claim 4 wherein in (b) the water miscible solvents are selected from the group consisting of methanol, ethanol, isopropyl, alcohol, propylene glycol, polyethylene glycol and glycerin.

7. The composition according to claim 5 wherein the water miscible solvents are selected from the group consisting of ethanol and glycerin.

8. The composition according to claim 7 wherein the aqueous solvent system comprises ethanol.

9. The composition according to claim 6 wherein the water miscible solvents are selected from the group consisting of ethanol and glycerin.

10. The composition according to claim 9 wherein the water miscible solvent is ethanol.

11. A transdermal flux enhancing pharmaceutical composition for transdermal administration to a human or animal subject comprising
(a) a safe and effective amount of a pharmacologically active compound selected from the group consisting of methyl salicylate, salicylic acid, ibuprofen, amlodipine, glipizide, doxazosin, piroxicam, a prodrug of piroxicam and pharmaceutically acceptable cationic and acid addition salts thereof;
(b) an aqueous solvent system comprising from about 30 to 75% by volume of one or more water miscible solvents; and
(c) from about 0.01 to 5% (w/v) of a penetration enhancer selected from a 1-alkylazacycloheptan-2-one, said alkyl having from 8 to 16 carbon atoms, and a cis-olefin compound of the formula

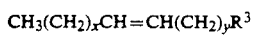

where $R^3$ is $CH_2OH$, $CH_2NH_2$ or $COR^4$ and $R^4$ is OH or $(C_1-C_4)$alkoxy, x and y are each an integer from 3 to 13 and the sum of x and y is from 10 to 16.

12. The composition according to claim 11 wherein in (b) the aqueous solvent system comprises from 30 to 60% by volume of one or more water miscible solvents.

13. The composition according to claim 11 wherein in (c) the penetration enhancer is a cis-monoenoic acid of the formula

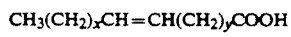

where x and y are as previously defined, or a 1-alkylazacycloheptan-2-one, said alkyl having from 10 to 14 carbon atoms.

14. The composition according to claim 13 wherein in (c) the penetration enhancer is cis-9-tetradecenoic acid, cis-6-pentadecenoic acid, cis-6-hexadecenoic acid, cis-9-hexadecenoic acid, cis-9-octadecenoic acid (oleic acid), cis-6-octadecenoic acid, cis-11-octadecenoic acid, cis-12-octadecenoic acid, cis-5-eicosenoic, cis-9-eicosenoic acid, cis-11-eicosenoic acid, cis-14-eicosenoic acid, 1-decylazacycloheptan-2-one, 1-dodecylazacycloheptan-2-one or 1-tetradecylazacycloheptan-2-one.

15. The composition according to claim 14 wherein the penetration enhancer is cis-9-octadecenoic acid (oleic acid), cis-11-octadecenoic acid or 1-dodecylazacycloheptan-2-one.

16. The composition according to claim 11 wherein in (b) the water miscible solvents are selected from the group consisting of methanol, ethanol, isopropyl, alcohol, propylene glycol, polyethylene glycol and glycerin.

17. The composition according to claim 16 wherein the water miscible solvents are selected from the group consisting of ethanol and glycerin.

18. The composition according to claim 17 wherein the water miscible solvent is ethanol.

19. The composition according to claim 12 wherein the water miscible solvent is ethanol.

20. The composition according to claim 15 wherein in (b) the water miscible solvents are selected from the group consisting of methanol, ethanol, isopropyl, alcohol, propylene glycol, polyethylene glycol and glycerin.

21. The composition according to claim 20 wherein the water miscible solvents are selected from the group consisting of ethanol and glycerin.

22. The composition according to claim 21 wherein the water miscible solvent is ethanol.

23. A transdermal flux enhancing pharmaceutical composition comprising
(a) a safe and effective amount of a pharmacologically active compound selected from the group consisting of methyl salicylate, salicylic acid, ibuprofen, amlodipine, glipizide, doxazosin, piroxicam, a prodrug of piroxicam of the formula

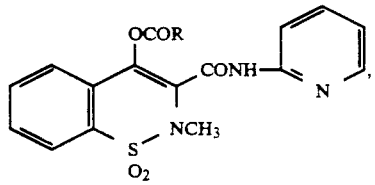

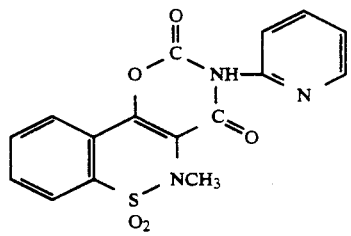

and pharmaceutically acceptable cationic and acid addition salts thereof;
where R is $C_1$ to $C_9$ straight chain or branched alkyl, $CH(R^1)OCOR^2$ and $R^1$ is H or $(C_1-C_3)$alkyl, and $R^2$ is $C_1-C_4$ alkyl or $C_1-C_4$ alkoxy;
(b) an aqueous solvent system comprising from about 30 to 75% by volume of one or more water miscible solvents; and
(c) from about 0.01 to 5% (w/v) of a penetration enhancer selected from the group consisting of a 1-alkylazacycloheptan-2-one, said alkyl having from 8 to 16 carbon atoms, and a cis-olefin compound of the formula

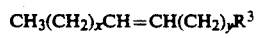

where $R^3$ is $CH_2OH$, $CH_2NH_2$ or $COR^4$ and $R^4$ is OH or $(C_1-C_4)$alkoxy, x and y are each an integer from 3 to 13 and the sum of x and y is from 10 to 16.

24. The composition according to claim 23 comprising (a) a safe and effective amount of piroxicam, the prodrug of piroxicam, or an acid addition salt thereof;
(b) an aqueous solvent system comprising from 30 to 60% by volume of ethanol; and
(c) 0.10 to 1.0% (w/v) cis-9-octadecenoic acid (oleic acid) or 1-dodecylazacycloheptan-2-one enhancer.

25. The composition according to claim 24 comprising
(a) piroxicam or the prodrug of piroxicam;
(b) an aqueous solvent system comprising from 30 to 50% by volume of ethanol; and
(c) 0.25 to 0.5% (w/v) cis-9-octadecenoic acid (oleic acid).

26. The composition according to claim 24 wherein the prodrug of piroxicam is of the formula

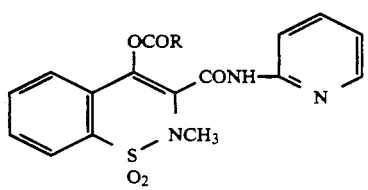

or

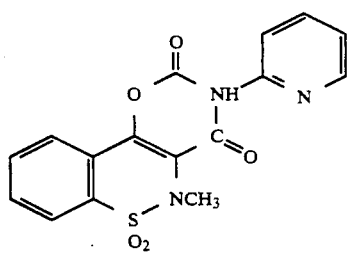

where R is $C_4$ to $C_6$ alkyl, $CH_2OCOC(CH_3)_3$ or $CH(CH_3)OCOC(CH_3)_3$.

27. The composition according to claim 11 comprising
(a) a safe and effective amount of amlodipine or an acid addition salt thereof;
(b) an aqueous solvent system comprising from 30 to 60% by volume of ethanol; and
(c) 0.10 to 1.0% (w/v) cis-9-octadecenoic acid (oleic acid) or 1-dodecylazacycloheptan-2-one as penetration enhancer.

28. The composition according to claim 11 comprising
(a) a safe and effective amount of methyl salicylate;
(b) an aqueous solvent system comprising from 30 to 75% by volume of ethanol; and
(c) 0.10 to 1.0% (w/v) cis-9-octadecenoic acid (oleic acid) as penetration enhancer.

29. A method of treating a rheumatic or inflammatory condition in a human or lower animal which comprises transdermally administratering to a human or animal in need of such treatment a safe and effective amount of a pharmacologically active compound selected from the group consisting of methyl salicylate, salicylic acid, ibuprofen, piroxicam, a prodrug of piroxicam and a pharmaceutically acceptable cationic and acid addition salt thereof, in an aqueous solvent system comprising from 30 to 75% by volume of one or more water miscible solvents and from 0.01 to 5% (w/v) of a penetration enhancer selected from a 1-alkylazacycloheptan-2-one, said alkyl having from 8 to 16 carbon atoms, and a cis-olefin compound of the formula

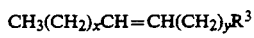

$$CH_3(CH_2)_xCH=CH(CH_2)_yR^3$$

where $R^3$ is $CH_2OH$, $CH_2NH_2$ or $COR^4$ and $R^4$ is OH or $(C_1-C_4)$alkoxy, x and y are each an integer from 3 to 13 and the sum of x and y is from 10 to 16.

30. The method according to claim 29 wherein the prodrug of piroxicam is of the formula

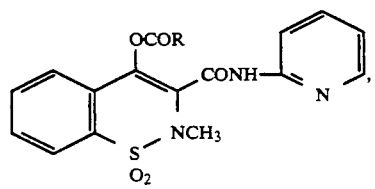

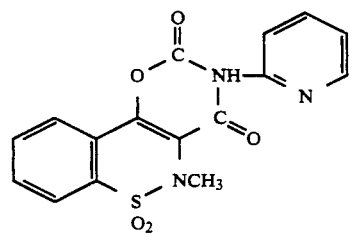

where R is $C_1$ to $C_9$ straight-chain or branched alkyl, $CH(R^1)OCOR^2$ and $R^1$ is H or $(C_1-C_3)$alkyl and $R^2$ is $(C_1-C_4)$alkyl or $(C_1-C_4)$alkoxy.

31. The method according to claim 29 wherein the pharmacologically active compound is piroxicam or a pharmaceutically acceptable acid addition salt thereof.

32. The method according to claim 31 wherein a saturated solution of piroxicam is employed, the solvent system comprises from 30 to 50% by volume of ethanol and the penetration enhancer is from 0.10 to 0.50% (w/v) cis-9-octadecenoic acid (oleic acid) or 1-dodecylazacycloheptan-2-one.

33. The method according to claim 29 wherein the aqueous solvent system comprises one or more water miscible solvents selected from the group consisting of methanol, ethanol, isopropyl alcohol, propylene glycol, polyethylene glycol and glycerin.

34. The method according to claim 33 wherein the water miscible solvents are selected from the group consisting of ethanol and glycerin.

35. A method for enhancing the transdermal administration of a physiologically active compound or prodrug thereof to a human or lower animal subject which comprises transdermally administering to said subject a pharmaceutical composition according to claim 1.

* * * * *

UNITED STATES PATENT AND TRADEMARK OFFICE
CERTIFICATE OF CORRECTION

PATENT NO. : 5,196,410
DATED      : March 23, 1993
INVENTOR(S): Michael L. Francoeur and Russell O. Potts It is certified that error appears in the above-identified patent and that said Letters Patent is hereby corrected as shown below:

At Column 3, line 9, "25/75" should read -- 15/85 --;

At Column 8, line 44, "(g/cm$^2$/hr)$^{(a)}$" should read -- ($\mu$g/cm$^2$/hr) $^{(a)}$ --;

At Column 8, line 51, the following should be inserted:

-- (a) Average of triplicate runs. Numbers in parentheses are from replicate experiments.

(b) Flux relative to that with 100% ethanol/0.25% v/v cis-9-octadecanoic acid (oleic acid). --;

At Column 9, line 37, "Ethanol" should read -- 55 Ethanol --;

At Column 11, line 8, "disintegration minute" should read -- disintegration per minute --;

Signed and Sealed this

Fourth Day of October, 1994

Attest:

BRUCE LEHMAN

Attesting Officer        Commissioner of Patents and Trademarks